US009116095B2

(12) United States Patent
Inoue et al.

(10) Patent No.: US 9,116,095 B2
(45) Date of Patent: Aug. 25, 2015

(54) METHOD OF INSPECTING WHEEL HUB UNIT

(71) Applicant: JTEKT CORPORATION, Osaka-shi, Osaka (JP)

(72) Inventors: Shigeru Inoue, Yokohama (JP); Kenjiro Matsumura, Osaka (JP); Masaki Yukawa, Osaka (JP)

(73) Assignee: JTEKT CORPORATION, Osaka (JP)

( * ) Notice: Subject to any disclaimer, the term of this patent is extended or adjusted under 35 U.S.C. 154(b) by 212 days.

(21) Appl. No.: 13/867,283

(22) Filed: Apr. 22, 2013

(65) Prior Publication Data

US 2013/0298680 A1    Nov. 14, 2013

(30) Foreign Application Priority Data

May 9, 2012    (JP) ................. 2012-107729

(51) Int. Cl.
    *G01N 29/04*    (2006.01)
    *B60B 27/00*    (2006.01)
    *G01M 13/04*    (2006.01)
    *G01N 29/14*    (2006.01)
    *G01N 29/44*    (2006.01)

(52) U.S. Cl.
    CPC ............ *G01N 29/04* (2013.01); *B60B 27/00* (2013.01); *B60B 27/0005* (2013.01); *G01M 13/045* (2013.01); *G01N 29/14* (2013.01); *G01N 29/4427* (2013.01); *B60B 27/0094* (2013.01); *B60B 2900/541* (2013.01); *B60B 2900/711* (2013.01); *G01N 2291/2696* (2013.01)

(58) Field of Classification Search
    CPC   B60B 27/00; B60B 27/0094; B60B 27/0005; B60B 2900/541; B60B 2900/711; G01N 29/04; G01N 29/14; G01N 2291/2696; G01N 29/4427; G01M 13/045
    USPC ............ 73/593, 114.81, 115.07, 660
    See application file for complete search history.

(56) References Cited

U.S. PATENT DOCUMENTS 5,072,611 A * 12/1991 Budd et al. ............... 73/115.07
5,557,854 A * 9/1996 Fujioka ......................... 33/517
(Continued)

FOREIGN PATENT DOCUMENTS

| EP | 2 306 170 A1 | 4/2011 |
| GB | 2 286 231 A | 8/1995 |
| JP | A-2010-25796 | 2/2010 |

OTHER PUBLICATIONS

Extended European Search Roport Issued in European Patent Application No. 13166398.1 on Sep. 16, 2013.

*Primary Examiner* — J M Saint Surin
(74) *Attorney, Agent, or Firm* — Oliff PLC

(57) ABSTRACT

In a method of inspecting a wheel hub unit configured by attaching a rolling bearing, which has an inner ring and an outer ring, to a hub wheel, an acoustic inspection dement is arranged so as to be in contact with an outer peripheral face of the outer ring, and the wheel hub unit (components except the outer ring) is rotated to measure an acoustic value of the outer ring and hence conduct inspection. When the wheel hub unit (components except the outer ring) is rotated, a preloading load that is equal to or higher than a load at which an axial internal clearance of the rolling bearing is a negative clearance is applied to the rolling bearing, and the axial internal clearance of the rolling bearing A is changed from a positive clearance before application of the load to a negative clearance after application of the load.

4 Claims, 4 Drawing Sheets

FIRST EMBODIMENT OF THE INVENTION

(56) References Cited

U.S. PATENT DOCUMENTS

| | | |
|---|---|---|
| 5,620,263 A | 4/1997 | Ohtsuki et al. |
| 2004/0022468 A1* | 2/2004 | Nomura et al. ............... 384/544 |
| 2004/0101223 A1* | 5/2004 | Baker et al. ................... 384/544 |
| 2006/0228060 A1* | 10/2006 | Inoue et al. ................... 384/448 |
| 2006/0239598 A1* | 10/2006 | Matsuyama et al. .......... 384/462 |
| 2009/0322171 A1* | 12/2009 | Wei et al. ........................ 310/90 |

* cited by examiner

FIRST EMBODIMENT OF THE INVENTION

FIRST EMBODIMENT OF THE INVENTION

SECOND EMBODIMENT OF THE INVENTION

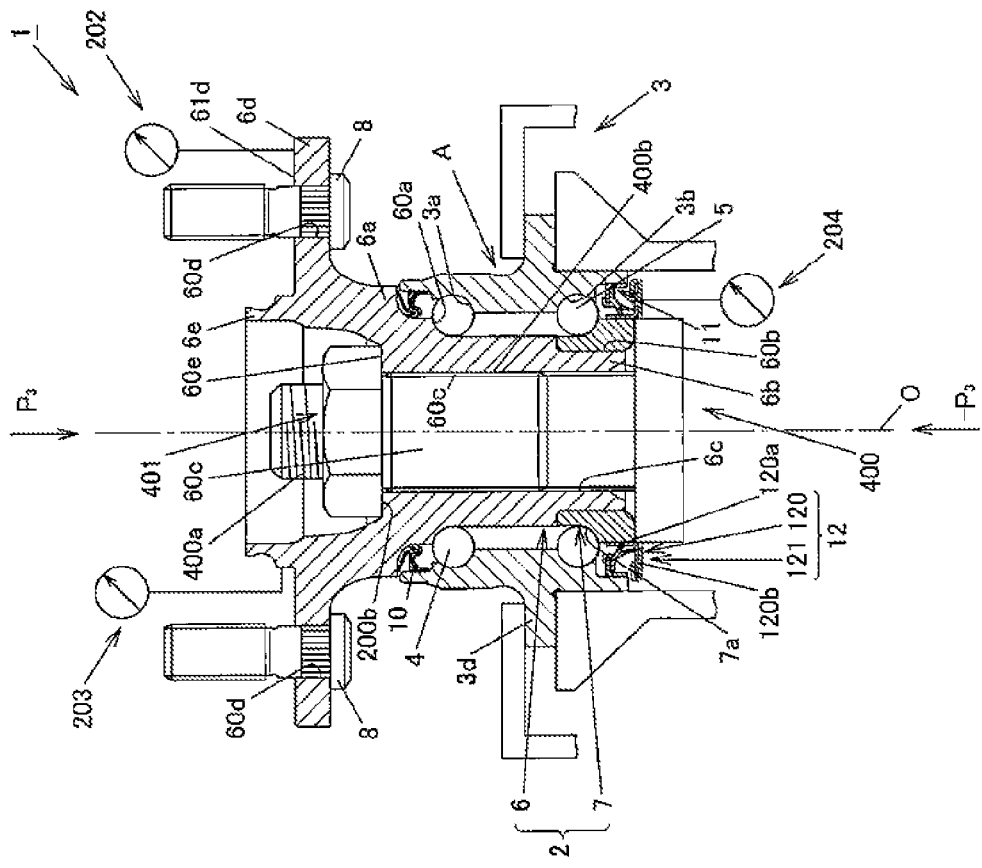

METHOD OF INSPECTING WHEEL HUB UNIT

INCORPORATION BY REFERENCE

The disclosure of Japanese Patent Application No. 2012-107729 filed on May 9, 2012 including the specification, drawings and abstract, is incorporated herein by reference in its entirety.

BACKGROUND OF THE INVENTION

1. Field of the Invention

The invention relates to a method of inspecting a wheel hub unit.

2. Description of the Related Art

In some wheel hub units, a hub wheel is fastened to a disc rotor and a wheel with bolts, and is rotatably attached to a vehicle body via a bearing.

In order to set a preload amount to a target value close to a preload of 0 (zero) after an axle is attached to a hub wheel (after an axial load is applied), a wheel hub unit as described above is shipped with the internal clearance of a bearing (rolling bearing that includes an inner ring, an outer ring, and rolling elements) set as a positive clearance (or a clearance between a negative clearance and a positive clearance). A "negative clearance" means an internal clearance of the rolling bearing in the case Where all the rolling elements of the rolling bearing roll between the inner ring and the outer ring. A "positive clearance" means an internal clearance of the rolling bearing in the case where the rolling elements of the rolling bearing slide between the inner ring and the outer ring.

Conventionally, a wheel hub unit of the above-described type is inspected by measuring the surface runout of a flange to which a wheel is attached, according to an inspection method using, for example, a dial gauge, at the time of shipment (see, for example, Japanese Patent Application Publication No. 2010-25796 (JP-2010-25796 A)).

With the aforementioned wheel hub unit including the bearing with a positive clearance, When an inspection object. which is a component of the wheel hub unit, is inspected an acoustic value and a flange surface runout are measured), a backlash may occur the bearing, resulting in a decrease in the reliability of inspection.

SUMMARY OF THE INVENTION

One object of the invention is to provide a method of inspecting a wheel hub unit, which makes it possible to suppress occurrence of a backlash of a bearing by reproducing a preload of the bearing at the time of inspection of an inspection object before the shipment of the wheel hub unit, thereby enhancing the reliability of inspection.

An aspect of the invention relates to a method of inspecting a wheel hub unit that is configured by attaching a bearing that has an inner ring and an outer ring to a hub wheel, in which an acoustic inspection element or a runout detection element is arranged at an inspected position of an inspection object as a component, which is different from a non-inspection object as a component other than the inspection object, the inspection object is inspected by rotating the inspection object or the non-inspection object in a case where the acoustic inspection element is used, and the inspection object is inspected by rotating the inspection object in a case where the runout detection element is used. According to the method, a preload is applied to the bearing. The preload is equal to or higher than a load at which an internal clearance as a moving distance in a case where one of the inner ring and the outer ring is fixed and the other one of the inner ring and the outer ring is moved in an axial direction is a negative clearance, and changing the internal clearance of the bearing from a. positive clearance before application of the preload to a negative clearance after application of the preload, when the inspection object or the non-inspection object is rotated.

BRIEF DESCRIPTION OF THE DRAWINGS

The foregoing and further features and advantages of the invention will become apparent from the following description of example embodiments with reference to the accompanying drawings, wherein like numerals are used to represent like elements and wherein:

FIG. 4 is a sectional view for illustrating a method of inspecting a wheel hub unit according to a modified example of the second embodiment of the invention.

DETAILED DESCRIPTION OF EMBODIMENTS

Hereinafter, embodiments of the invention will be described in detail with reference to the accompanying drawings.

Figure 1:
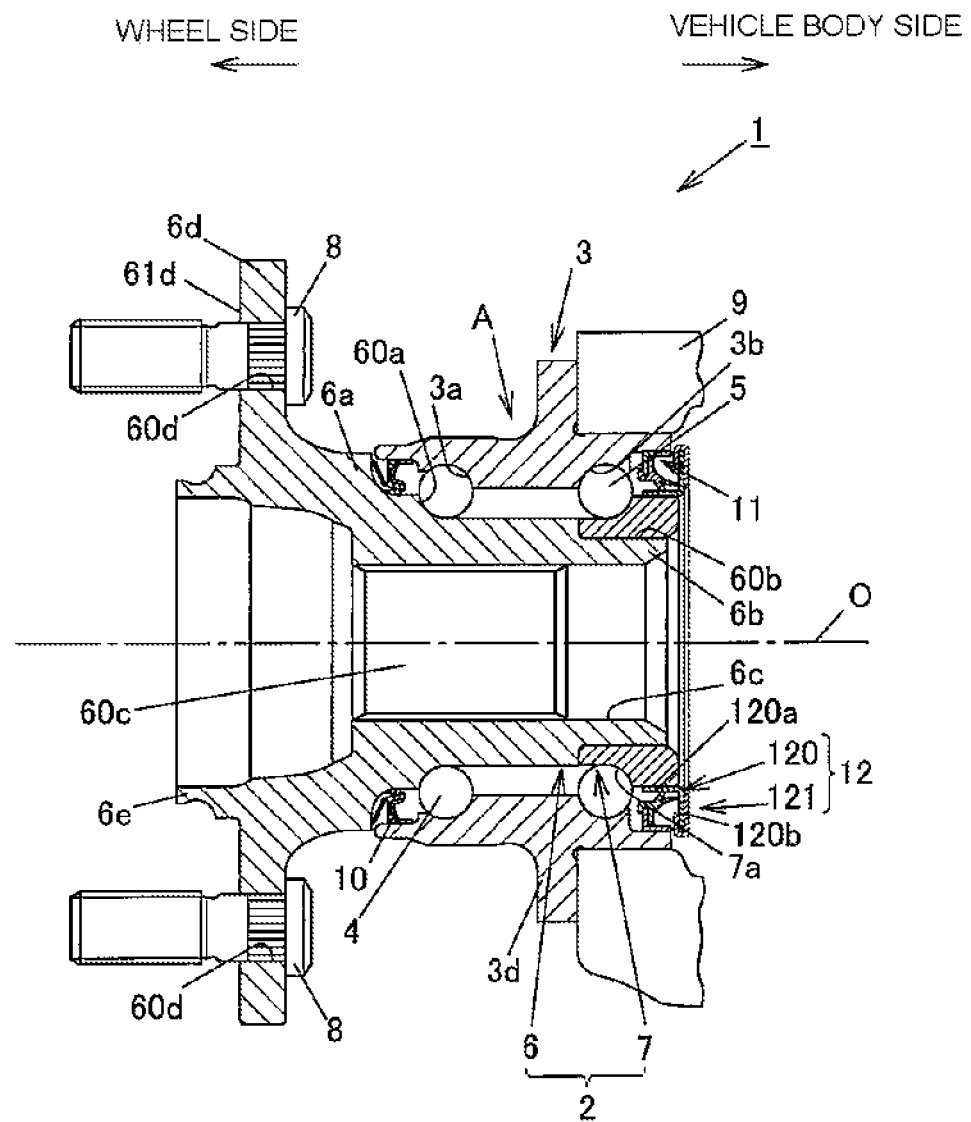
FIG. 1 is a sectional view showing the entirety of a wheel hub unit that is used in a method of inspecting a wheel hub unit according to a first embodiment of the invention.

FIG. 1 shows the entirety of a wheel hub unit 1. As shown in FIG. 1, the wheel hub unit 1 is configured as, for example, a drive wheel hub unit. The wheel hub unit 1 includes an inner member 2, an outer member (an outer ring) 3, and double-row rolling elements 4, 5. The wheel hub unit 1 is arranged between a vehicle body (not shown) and a wheel not shown). A hub wheel 6 of the wheel hub unit 1 is rotatably supported by a member on the vehicle body side (inner side in the vehicle lateral direction: right side in FIG. 1) via a rolling bearing to ball bearing) A. The rolling bearing A includes an inner ring 7, the outer ring 3, and the rolling elements 4, 5. The rolling bearing A is attached to the hub wheel 6. The rolling bearing A constitutes the wheel hub unit 1 together with sealing members 10, 11 and a slinger 120 of a pulser ring 12.

The inner member 2 is formed of the hub wheel 6 and the inner ring 7. The inner member 2 is rotatably arranged on a central axis O.

The hub wheel 6 has trunk portions 6a, 6b (the large-diameter trunk portion 6a and the small-diameter trunk portion 6b). The hub wheel 6 is coupled to a drive shaft (not shown) via a constant. velocity universal joint (not shown) or the like in such a manner that torque is transmittable therebetween. The hub wheel 6 is fastened to the constant velocity universal joint with a nut. The hub Wheel 6 is formed of a cylindrical compact that is made of, for example, medium carbon steel. A through-hole 6c that extends along the central axis O and opens toward both sides in the central axis O is formed in the hub wheel 6. Serrations (splines) 60c for coupling a stem (not shown) of the constant velocity universal joint to the hub wheel 6 are formed on an inner peripheral portion of the hub wheel 6 that defines the through-hole 6c.

The large-diameter trunk portion 6a has an inner raceway surface 60a on its outer peripheral face. On the inner raceway surface 60a, the rolling elements 4 in the wheel-side row (the left side in FIG. 1), among the double-row rolling elements 4, 5, roll. The large-diameter trunk portion 6a is located at a wheel side portion of the hub wheel 6. The large-diameter trunk portion 6a is integrally formed with an annular wheel attachment flange 6d which protrudes from the outer peripheral thee of the large-diameter trunk portion 6a and to which the wheel (not shown) is attached. The wheel attachment flange 6d has a plurality of bolt insertion holes 60d (only two of which are shown) which is arranged in the circumferential direction and through which hub bolts 8 are passed. The outer diameter of the large-diameter trunk portion 6a is set larger than the outer diameter of the small-diameter mink portion Ob. The large-diameter trunk portion 6a has a spigot portion 6e that protrudes from a wheel-side end face thereof The small-diameter trunk portion Oh has a recessed attachment face 60b to which the inner ring 7 is attached, on its outer peripheral face. The small-diameter trunk portion Ob is inserted into the inner ring 7, and is located at a vehicle body side portion (on the right side in FIG. 1) of the hub wheel 6.

On the other hand, the inner ring 7 has an inner raceway surface 7a on which the rolling elements 5 in the vehicle body-side row, among the double-row rolling elements 4, 5, roll. The inner ring 7 is press-fitted to and attached to the attachment face 60b of the small-diameter trunk portion 6b. The inner wheel 7 is formed of a cylindrical compact that is made of for example, bearing steel. The pulser ring 12 that detects a rotational speed of the hub wheel 6 (the inner ring 7) is arranged at a vehicle body-side end of the inner ring 7.

The pulser ring 12 has the slinger 120 and a magnetized rubber piece 121. The slinger 120 is formed of a steel annular member that is constituted of a cylindrical portion 120a and an annular portion 120b. The slinger 120 is press-fitted to and attached to an outer peripheral face of the vehicle body-side end of the inner ring 7. The magnetized rubber piece 121 is adhesively joined to the annular portion 120b of the slinger 120 through, for example, vulcanization. The magnetized rubber piece 121 is formed by mixing, for example, ferrite stainless steel powder into an annular rubber member and forming north poles and south poles at equal intervals in the circumferential direction through magnetization.

The outer ring, 3 has a first outer raceway surface 3a and a second outer raceway surface 3b. On the first outer raceway surface 3a, the rolling elements 4 in the wheel-side row, among the double-row rolling elements 4, 5, roll. On the second outer raceway surface 3b, the rolling elements 5 in the vehicle body-side row roll. The outer ring 3 is attached to a vehicle body side member via a knuckle 9 that serves as a component of a suspension system (not shown). The outer ring 3 is formed of a cylindrical compact that opens toward both sides in the central axis O and that is made of, for example, medium carbon steel. The outer ring 3 is integrally formed with an annular vehicle body attachment flange 3d that protrudes from an outer peripheral face thereof. The vehicle body attachment flange 3d has a plurality of bolt insertion holes (not shown) which is arranged in the circumferential direction and through which knuckle bolts (not shown) are passed.

Each of the rolling elements 4 in one-side (wheel-side) row is configured as a steel ball. The rolling elements 4 in the wheel-side row are arranged so as to be interposed between the inner raceway surface 60a of the hub wheel 6 and the first outer raceway surface 3a of the outer ring 3. The rolling elements 4 in the wheel-side row are rollably held by a ball cage (not shown). The wheel-side sealing member 10 that is interposed between an outer peripheral face of the hub wheel 6 and an inner peripheral face of the outer ring 3 is arranged on the wheel side of the rolling elements 4 in the wheel-side row.

Each of the rolling elements 5 in the other-side (vehicle body-side) row is configured as a steel ball. The rolling elements 5 in the vehicle body-side row are arranged so as to be interposed between the inner raceway surface 7a Of the inner ring 7 and the second oilier raceway surface 3b of the outer ring 3. The rolling elements 5 in the vehicle body-side row are rollably held by a ball cage (not shown). The vehicle body-side sealing member 11 that is interposed between an enter peripheral face of the pulser ring 12 (the cylindrical portion 120a of the slinger 120) and the inner peripheral face of the outer ring 3 is arranged on the vehicle body side of the rolling elements 5 in the vehicle body-side row.

An operation of the wheel hub unit 1 illustrated in the present embodiment is performed in the same manner as that of the operation of conventional wheel hub units. That is, when torque is transmitted from an engine side of a vehicle to the hub wheel 6 via the constant velocity universal joint or the like, the huh wheel 6 rotates together with the inner ring 7. Because the wheel is attached to the hub wheel 6, the torque from the engine side is transmitted also to the wheel, and the wheel rotates together with the hub wheel 6.

Figure 2:
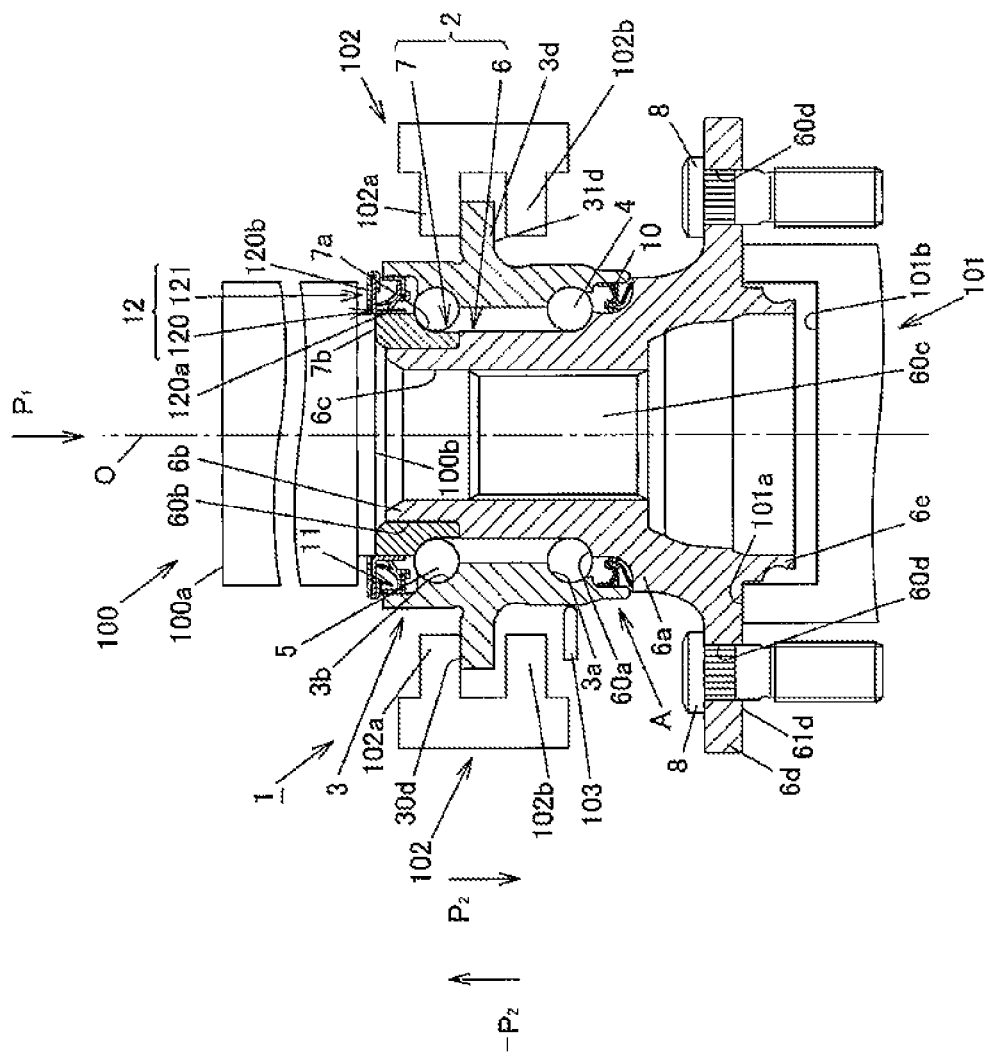
FIG. 2 is a sectional view for illustrating the method of inspecting a wheel hub unit according to the first embodiment of the invention.

Next, a method of inspecting the wheel hub unit 1 illustrated in the present embodiment will be described with reference to FIG. 2. FIG. 2 shows the method of inspecting the wheel hub unit 1.

The method of inspecting the wheel hub unit 1 illustrated in the present embodiment is carried out as shown in FIG. 2. First, the hub wheel 6 and the inner ring 7 are held by a pair of jigs 100, 101 (the upper jig 100 and the lower jig 101). Subsequently. a clamp load $P_1$ is applied to the upper jig 100 in the direction toward the lower jig 101, and a preloading load $P_2$ is applied to the outer ring 3 as an inspection object, which is a component of the wheel hub unit 1, downward (toward the vehicle body attachment flange 3d) along the direction of the axis (the central axis O) by a load application member 102. Before application of the preloading load $P_2$ to the outer ring 3, the axial internal clearance of the rolling hearing A is a positive clearance. After application of the preloading load $P_2$ to the outer ring 3, the axial internal clearance of the rolling bearing A is a negative clearance. An "axial internal clearance" means an internal clearance as a moving distance in the case where one of the inner ring 7 and the outer ring 3 is fixed and the other one of the inner ring 7 and the outer ring 3 is moved in the axial direction. The loads $P_1$, $P_2$ are applied with the lower jig 101 arranged at a. fixed position in the axial direction (in the direction of the central axis O). After that, an acoustic inspection element 103 is brought into contact with the outer peripheral face (an inspected position) of the outer ring 3, and the lower jig 101 is rotated, together with non-inspection objects (components of the wheel hub unit 1 except the outer ring 3) and the upper jig 100, about the central axis O at a speed of, for example, 1000 to 2000 rpm. Each of $P_1$, $P_2$ represents the magnitude of load.

In this case, the clamp load $P_1$ is applied to the upper jig 100 via a thrust bearing (not shown) or the like. The preloading load $P_2$ is applied to the vehicle body attachment flange 3d of the outer ring, 3 via the load application member 102, in the same direction as the direction of the clamp load $P_1$. The clamp load $P_1$ may be either higher or lower than the preloading load $P_2$, or may be equal in magnitude to the preloading load $P_2$. The preloading load $P_2$ is set equal to or higher than a load at which the axial internal clearance of the rolling bearing A is a negative clearance. A magnitude of the preloading load $P_2$ and a decrease in the axial internal clearance of the rolling bearing A are measured and a correlation between the measured values are stored in advance in the form of data. The preloading load $P_2$ is determined on the basis of the correlation stored in the form of data.

In the method of inspecting the wheel hub unit 1, a pressing member, which has a receiving face 100a that receives the clamp load $P_1$ and a pressing face 100b that is pressed against a vehicle body-side end face 7b of the inner ring 7, is used as the upper jig 100. A rotary member, which has an end bee 101a that contacts an end face 6d of the wheel attachment flange 6d of the hub wheel 6 and an opening portion 101b capable of accommodating the spigot portion 6e of the hub wheel 6 and which is rotated by for example, a motor (not shown), is used as the lower jig 101. A movable member, which has a pressing portion 102a that applies the preloading load $P_2$ to an end face 30d of the vehicle body attachment flange 3d of the outer ring 3 and a pressing portion 102b that applies a preloading load —$P_2$ to an end face 31d of the vehicle attachment flange 3d of the outer ring 3, is used as the load application member 102. As the acoustic inspection element 103, for example, a speed type sensor is used.

Thus, it is possible to measure an acoustic value of the wheel hub unit 1 by detecting a frequency that is transmitted from the non-inspection objects to the outer ring 3. If the frequency detected by the acoustic inspection element 103 is equal to or higher than a prescribed value (an NG frequency), the wheel hub unit 1 is regarded as a defective product. If the frequency detected by the acoustic inspection element 103 is lower than the NG (not good) frequency. the wheel hub unit 1 is regarded as a conforming product.

According to the first embodiment described above, the following advantageous effect is obtained.

The axial internal clearance of the rolling bearing A is changed from a positive clearance before application of the preload to a negative clearance after application of the preload. Thus, it is possible suppress a backlash of the rolling bearing A by reproducing the preload of the rolling bearing A at the time of inspection of the inspection object before the shipment of the wheel hub unit 1, thereby enhancing the reliability of inspection.

In the present embodiment, the case where the pressing portion 102a of the load application member 102 applies the preloading load $P_2$ to the end face 30d of the vehicle body attachment flange 3d of the outer ring 3 has been described. However, the invention is not limited to this The pressing portion 102b of the load application member 102 may apply the preloading load —$P_2$ ($|-P_2|=|P_2|$) to the end face 31d of the vehicle body attachment flange 3d of the outer ring 3. In this case, if the preloading load $|-P_2|$ is set higher than the clamp load $|P_1|$, it is difficult to conduct inspection due to the movement of the entire wheel hub unit 1 in the direction of the preloading load $|-P_2|$. Therefore, the preloading load $|-P_2|$ needs to be lower than $|P_1|$ ($|-P_2|<|P_1|$). The load $P_2$ indicates a downward load. The load $-P_2$ indicates an upward load.

In the present embodiment, the case where the Wheel hub unit 1 is inspected (the acoustic value is measured) by rotating the components of the wheel hub unit 1 except the outer ring 3 has been described. However, the invention is not limited to this. The acoustic value may be measured by rotating the outer ring 3.

In the present embodiment, the case where the acoustic value of the outer ring 3 is measured to inspect the wheel hub unit 1 has been described. However, the invention is not limited to this The wheel hub unit 1 ma be inspected by measuring runout values of the hub wheel 6 the wheel attachment flange 6d and the spigot portion 6e) and the slinger 120 (the sealing member 11).

Figure 3:
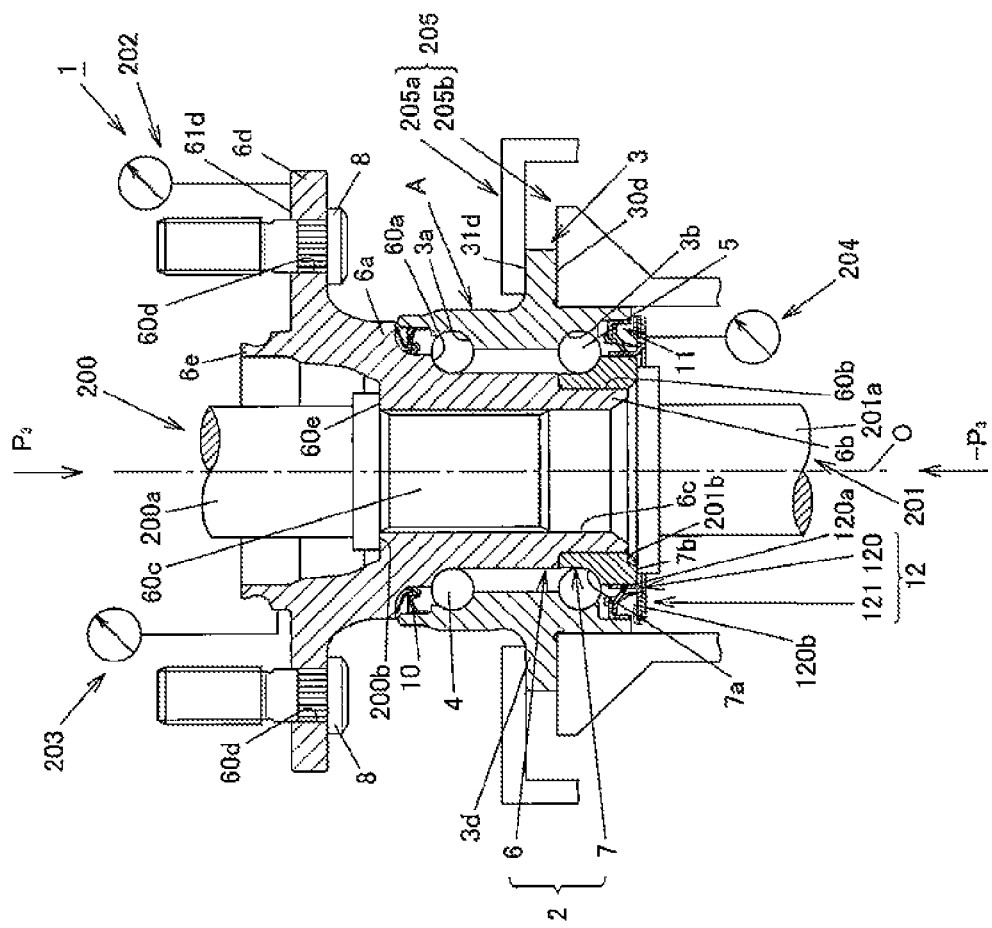
FIG. 3 is a sectional view for illustrating a method of inspecting a wheel hub unit according to a second embodiment of the invention.

Next, a method of inspecting the wheel hub unit 1 illustrated in a second embodiment of the invention will be described with reference to FIG. 3. FIG. 3 shows the method of inspecting the wheel hub unit 1.

The method of inspecting the wheel hub unit 1 illustrated in the present embodiment is carried out as shown in FIG. 3. First, the outer ring 3 as a non-inspection object, which is a component other than inspection objects as components in the wheel hub unit 1, is held by a holder (a jig) 205. Subsequently, a preloading load $P_3$ (a downward load) and a preloading load $-P_3$ (an upward load) are applied to the huh wheel 6 and the inner ring 7 by a pair of jigs 200, 201 (an upper jig 200 and a lower jig 201), respectively. After that, runout detection elements 202, 203, 204 are brought into contact with the hub wheel 6 (the end face 61d of the wheel attachment flange 6d and the outer peripheral face of the spigot portion 6e) and the pulser ring 12 the end thee of the annular portion 120b of the stinger 120) as inspection objects, respectively and the upper jig 200 and the lower jig 201 are synchronized with each other and rotated together with the inspection objects (the components of the wheel hub unit 1 except the outer ring 3) by 360°. In this case, the runout detection element 202 is arranged so as to be in contact with the end face 61d of the wheel attachment flange 6d. The runout detection element 203 is arranged so as to he in contact with the outer peripheral face of the spigot portion 6e. The runout detection element 204 is arranged so as to be in contact with the end face of the annular portion 120b of the slinger 120. $P_3$ represents the magnitude of load.

In this case, the preloading load $P_3$ is applied to the upper jig 200. A preloading load $-P_3$ ($|-P_3|=|P_3|$) is applied to the lower jig 201. Each of the preloading loads $P_3$, $-P_3$ is set equal to or higher than a load at which the axial internal clearance of the rolling bearing A is a negative clearance. A magnitude of each of the preloading loads $P_3$, $-P_3$ and a decrease in the axial internal clearance of the rolling bearing A are measured and a correlation between the measured values are stored in advance in the form of data. The preloading loads $P_3$. $-P_3$ are determined on the basis of the correlation stored in the form of data. The load $P_3$ indicates a downward load. The load $-P_3$ indicates an upward load.

In the method of inspecting the wheel hub unit 1, a rotary member is used as the upper jig 200. The rotary member has a shaft portion 200a that receives the preloading load $P_3$ and a pressing face 200b that is pressed against a wheel-side end face (an end face on which a nut abuts in the case where the wheel hub unit 1 is fastened to a constant velocity universal joint with the nut) 60e of the through-hole 6c of the hub wheel 6. The rotary member is rotated by, for example, a motor (not shown). A rotary member, which has a shaft portion 201a that receives the preloading, load $-P_3$ and it pressing face 201b that is pressed against the vehicle body-side end face 7b of the inner ring 7 and is rotated by, for example, a motor (not shown), is used as the lower jig 201. The holder 205 has finger portions 205a, 205b that retain the vehicle body attachment flange 3d of the outer ring 3. A movable member that moves in the direction of the central axis O is used as at least one member among the finger portions 205a, 205b (e.g., the finger portion 205a).

Thus, the runout of the hub wheel 6 (the wheel attachment flange 6d and the spigot portion 6e) and the slinger 120 (the sealing member 11) as inspection objects are measured. If the runout value detected by the runout detection elements 202, 703, 204 is equal to or larger than a prescribed value (an NG runout value), the wheel hub unit 1 is regarded as a defective product. If the runout value detected by the runout detection elements 202, 203, 204 is smaller than the NG runout value, the wheel hub unit 1 is regarded as a conforming product.

According to the second embodiment of the invention described above, the following advantageous effect is obtained.

The axial internal clearance of the rolling bearing A is changed from a positive clearance before application of the preload to a negative clearance after application of the preload. Thus, it is possible to suppress occurrence of a backlash of the rolling bearing A by reproducing the preload of the rolling bearing A at the time of inspection of the inspection objects before the shipment of the wheel hub unit 1, thereby enhancing the reliability of inspection.

In the present embodiment of the invention, the case where the pan of the jigs 200, 201 is used when the preload is applied to the hub wheel 6 and the inner ring 7 has been described. However, the invention is not limited to this. Instead of the pair of the jigs 200, 201, a bolt 400 and a nut 401 may be used as another pair of jigs as shown in FIG. 4. In this case, the bolt 400 has a threaded portion 400a that is screwed to the nut 401, and serrations (splines) 400b that are fitted to the serrations 60c of the hub wheel 6. At the time of inspecting the wheel hub unit 1, the hub wheel 6, the inner ring 7, and the like rotate together with the bolt 400 and the nut 401, with the outer ring 3 held. Thus, no rotary torque is transmitted from the serrations 400b of the bolt 400 to the serrations 60c of the hub wheel 6, so that the serrations 60c of the hub wheel 6 are not damaged.

In the present embodiment of the invention, the case where the runout values of the hub wheel 6 (the Wheel attachment flange 6d and the spigot portion 6e) and the slinger 120 (the sealing member 11) are measured to inspect the wheel hub unit 1 has been described. However, the invention is not limited to this. The wheel hub unit 1 may also be inspected by measuring an acoustic value of the outer ring 3.

The method of inspecting the wheel hub unit according to the invention has been described above on the basis of the foregoing embodiments. However, the invention is not limited to the foregoing embodiments, and may be carried out in various. other embodiments without departing from the scope of the invention. For example, the following modifications may be made.

(1) In each of the foregoing embodiments of the invention, the case where the runout detection element 204 is brought into contact with the slinger 120 of the pulser ring 12 to measure the runout value of the sealing member 11 has been described. However, the invention is not limited to this. The runout value of the magnetized rubber piece 121 may also be measured by bringing the runout detection element 204 into contact with the magnetized rubber piece 121 of the pulser ring 12.

(2) in each of the foregoing embodiments of the invention, the case where the speed type sensor is used as an example of the acoustic detection element 103 has been described. However, the invention is not limited to tins, Another contact type sensor such as an acceleration type sensor or the like may also be used. In addition, for example, a noncontact type sensor such as an ultrasonic sensor or the like may also be used as the acoustic inspection element, instead of the contact type sensor.

(3) In each of the foregoing embodiments of the invention, the case where the invention is applied to the drive wheel hub unit has been described. However, the invention is not limited to this. The invention is also applicable to a driven wheel hub unit in the same manner as that in the foregoing embodiments of the invention.

According to the invention, it is possible to suppress occurrence of a backlash of the bearing b reproducing the preload of the bearing at the time of inspection of the inspection object before the shipment of the wheel hub unit, thereby enhancing the reliability of inspection.

What is claimed is:

1. A method of inspecting a wheel hub unit that is configured by:
   attaching a bearing that has an inner ring and an outer ring to a hub wheel,
   arranging an acoustic inspection element or a runout detection element at an inspected position of an inspection object as a component, which is different from a non-inspection object as a component other than the inspection object,
   inspecting the inspection object by rotating the inspection object or the non-inspection object in a case where the acoustic inspection element is used, and
   inspecting the inspection object by rotating the inspection object in a case where the runout detection element is used, the method of inspecting the wheel hub unit comprising the steps of:
   applying, to the bearing, a preload that is equal to or higher than a load at which an internal clearance is a negative clearance, wherein:
   a first inner ring and a first outer ring are fixed,
   a second inner ring and a second outer ring are movable, and
   the internal clearance is an axial moving distance of the second inner ring and the second outer ring; and
   changing the internal clearance of the bearing from a positive clearance before application of the preload to a negative clearance after application of the preload, when the inspection object or the non-inspection object is rotated.

2. The method of inspecting the wheel hub unit according to claim 1, wherein the inspection is conducted by retaining the inner ring and the hub wheel by a pair of jigs, subsequently applying a clamp load to one of the jigs in a direction toward the other jig, applying a preloading load to the outer ring along the axial direction, and then rotating the other jig.

3. The method of inspecting the wheel hub unit according to claim 1, wherein the inspection is conducted by holding the outer ring by a jig, subsequently applying a preloading load to the inner ring and the hub wheel along the axial direction by a pair of jigs other than the jig, and then rotating the pair of the jigs.

4. The method of inspecting the wheel hub unit according to claim 3, wherein the pair of the jigs are a bolt having an outer peripheral face that is spline-fitted to an inner peripheral face of the hub wheel, and a nut that is screwed to the bolt.

* * * * *